United States Patent [19]

Maeda et al.

[11] 3,933,587
[45] Jan. 20, 1976

[54] METHOD FOR PRODUCTION OF IMMOBILIZED ENZYME

[75] Inventors: Hidekatsu Maeda, Chiba; Aizo Yamauchi, Yokohama; Hideo Suzuki; Akira Kamibayashi, both of Chiba, all of Japan

[73] Assignee: Agency of Industrial Science & Technology, Tokyo, Japan

[22] Filed: Nov. 23, 1973

[21] Appl. No.: 418,264

[30] Foreign Application Priority Data
Dec. 7, 1972    Japan.............................. 47-122860

[52] U.S. Cl. ............. 195/68; 195/63; 195/DIG. 11; 260/8; 204/159.14
[51] Int. Cl................................................ C07g 7/02
[58] Field of Search................ 195/68, 63, DIG. 11; 260/8

[56] References Cited
UNITED STATES PATENTS
3,788,950    1/1974    Hicks et al........................ 195/63 X FOREIGN PATENTS OR APPLICATIONS
1,955,638    6/1970    Germany..................... 195/DIG. 11

Primary Examiner—Lionel M. Shapiro
Attorney, Agent, or Firm—Oblon, Fisher, Spivak, McClelland & Maier

[57]    ABSTRACT

Immobilized enzymes are produced by adding radioresistant enzymes to 5–25% aqueous solutions of polyvinyl type high molecular compounds and irradiating the enzyme-containing solutions with a high dosage of ionizing radiant rays in an inert atmosphere or under a decreased pressure for thereby gelling said solutions.

5 Claims, No Drawings

METHOD FOR PRODUCTION OF IMMOBILIZED ENZYME

BACKGROUND OF THE INVENTION

This invention relates to a method for the production of immobilized enzymes, and more particularly to a method for the production of immobilized enzymes, which comprises irradiating aqueous solutions of polyvinyl type high molecular compounds containing enzymes with ionizing radiant rays for thereby gelling said solutions.

In a reaction using an enzyme, handling of the enzyme is facilitated if the enzyme is available in a solidified form. For the immobilization of enzymes, numerous methods have to date been proposed. Of the various methods heretofore proposed, typical are a method which consists in joining an enzyme to a water-immobilized carrier, a method which causes the enzyme to be encapsulated with a water-immobilized high molecular substance and a method which comprises combining two enzymes with each other and gelling to immobilize the resultant mixture.

Since the methods proposed to date are highly complicated and use expensive substances, their production costs are too high for the methods to be practicable. Such is the true state of affairs.

The primary object of this invention, therefore, is to provide a method for the production of an immobilized enzyme, which permits the immobilization of enzyme to be accomplished completely and economically by a simple process.

SUMMARY OF THE INVENTION

To accomplish the aforementioned object, the method for the production of an immobilized enzyme according to this invention comprises the steps of adding a given enzyme to an aqueous solution of polyvinyl alcohol or an aqueous solution of polyvinyl pyrrolidone and, in an inert atmosphere or under a decreased pressure, irradiating the enzyme-containing solution with ionizing radiant rays for thereby gelling the solution. When the aqueous solution of polyvinyl alcohol or the aqueous solution of polyvinyl pyrrolidone is irradiated with ionizing radiant rays as described above, the hydrogen atoms attached to the carbon atoms which are coupled with the hydroxyl group or pyrrolidone group are thrown out of position to give rise to radicals, with the result that the high molecular compound undergoes cross linking. Consequently, the enzyme is immobilized as it is entrapped within the high molecular lattice formed. The degree of cross-linking involved in this case is pronouncedly high as compared with the degree achievable by the conventional method using a cross-linker, so that the product suffers from very little or absolutely no leakage of enzyme.

The method of this invention is economical, for it uses polyvinyl alcohol or polyvinyl pyrrolidone which is an inexpensive organic high molecular material. In terms of operation, this method is simple because it only requires irradiation of the enzyme-containing solution with radiant rays.

Other objects and other characteristics of this invention will become apparent for the further disclosure of this invention to be given herein below.

DETAILED DESCRIPTION OF THE INVENTION

It has heretofore been known to produce an immobilized enzyme having the enzyme entrapped with a water-immobilized gelled high molecular compound. This method comprises adding the enzyme to an aqueous solution of acrylamide and N-bis-methylene acrylamide as a cross-linker and polymerizing the enzyme-containing solution in the presence of potassium persulfate, dimethyl amino propionitrile, etc. added thereto as polymerization accelerators or gelling said solution by the irradiation with gamma rays. This method inevitably involves the use of an expensive cross-linker in order to have the enzyme entrapped with the lattice of high molecular compound. When the inventors tried immobilization of glucoamylase and adenyl deaminase by this method, however, the enzymes partly leaked from the immobilized products. Although they tried various measures to preclude this leakage of enzymes, no perfect prevention of the leakage could be attained. Recent reports indicate that the leakage of enzymes occurs, though to limited extent, even in the case of techniques utilizing radiant rays. Thus, it has been extremely difficult to have enzymes completely entrapped in the lattices of gelled high molecular compounds, with the aid of cross-linkers.

In view of the true state of affairs mentioned above, the inventors pursued various studies to find a method for immobilizing enzymes by using, as media, such inexpensive organic high molecular materials as polyvinyl alcohol and polyvinyl pyrrolidone. As a consequence, they have made the discovery that while, in the conventional mobilization of enzymes by irradiation with radiant rays, the highest dosage or radiant rays heretofore accepted as permissible from the standpoint of the stability of enzymes has been on the order of 40,000 to 50,000 rad, enzymes are sufficiently stable to high dosage of ionizing radiant rays so far as they are held in aqueous solution containing polyvinyl alcohol. This discovery has further led to completion of a producing immobilized enzymes having enzymes entrapped with polyvinyl alcohol by irradiating aqueous solutions of polyvinyl alcohol incorporating the enzymes with a high dosage of ionizing radiant rays. Thus, the present invention has been accomplished.

The polyvinyl alcohol to be used for the present invention may be any of the products which are obtained by partial and complete hydrolysis of polyvinyl acetate. The polyvinyl alcohol may partially contain acetic ester residue. In the case of polyvinyl pyrrolidone, not every vinyl group present therein is required to contain a pyrrolidone group. THe polyvinyl alcohol may contain such other water-mobilized monomer as acrylamide. This polyvinyl type high molecular compound is used in the form 2 – 40% aqueous solution. Any polyvinyl alcohol concentration below 2% is impracticable because the gelled product to be obtained consequently shrinks too much to satisfy the object of this invention.

All enzymes which are stable to ionizing radiant rays irradiated at a dosage up to several M.rads in the presence of polyvinyl alcohol can be immobilized by the method of this invention. Examples of the enzymes satisfying this requirement include glucoamylase, invertase, beta-galactosidase, glucose oxidase, glucose isomerase and catalase. The amount in which the enzyme is added to the aqueous solution of polyvinyl type high molecular compound is in the range of from 0.001 to 5% by weight. Although this amount is variable with the kind of enzyme to be immobilized, no perfect immobilization can be accomplished if the amount exceeds the upper limit of said range.

The enzyme solution prepared as described above is then irradiated with ionizing radiant rays so as to be gelled. Examples of the radiant rays suitable for this purpose are beta rays and gamma rays. Besides, accelerated electron rays may be used. The optimum dosage of such radiant rays is such that the absorbency falls in the range of from 1 M.rads to 20 M.rads. The irradiation is best carried out in an atmosphere devoid of oxygen, such as in nitrogen atmosphere or under a decreased pressure.

DESCRIPTION OF THE PREFERRED EMBODIMENT

Now, preferred embodiments of the present invention will be described. First, a polyvinyl type high molecular compound such as polyvinyl alcohol or polyvinyl pyrrolidone is dissolved in water heated in an inert atmosphere to produce a 2 – 40% aqueous solution. After the solution is cooled, an enzyme solution is added to the aqueous solution in an amount to give an enzyme content of from 0.001 to 5% based on the weight of the aqueous solution of polyvinyl type high molecular compound. The mixture is thoroughly stirred, placed in an ampoule and sealed hermetically under a decreased pressure or in an inert atmosphere. In this case, it is desired to have the mixture incorporate a highly diluted buffer solution prior to sealing so as to preclude possible variation of its hydrogen ion concentration (pH). Then, the sealed ampoule is irradiated with ionizing radiant rays such as, for example, gamma rays and accelerated electron rays. At the end of the irradiation, the gelled contents are removed from the ampoule and finely divided. The finely divided gel is used as desired on a given substrate as by being placed in a column, for example. The results of immobilization obtained in this case are comparable with those obtainable by immobilization with the use of acrylamide described above. And the gelled product is shown to be usable satisfactorily as an immobilized enzyme. While a slight degree of enzyme leakage is observed to occur in the immobilized enzyme prepared by the use of acrylamide, no enzyme leakage is observed at all in the product obtained by the method of this invention. This perfect elimination of enzyme leakage may possibly be explained by postulating that the irradiation of the aqueous solution of polyvinyl type high molecular compound with a large dosage of radiant rays gives a higher degree of cross-linking than by the conventional method whereby the enzyme is entrapped with a high molecular compound.

Further, the immobilized enzyme formed with polyvinyl alcohol gel or polyvinyl pyrrolidone gel, unlike the product using acrylamide gel, has little possibility of inducing foreign-body reaction on the living cells and, therefore, can sufficiently be utilized for pharmaceutical applications.

As described above, the method according to this invention provides thorough immobilization of enzymes by using, as media, such inexpensive organic high molecular materials as polyvinyl alcohol. In view of today's widespread utility of radiant rays energy, therefore, the method of this invention enables enzymes to be very easily and economically immobilized, making a great contribution to industries utilizing enzymes.

Now, working examples of the present invention will be described hereinafter. It should be understood, however, that the present invention is not limited in any sense to the following examples.

EXAMPLE 1

In a nitrogen atmosphere, 10 g of polyvinyl alcohol was dissolved under heating in 90 ml of water saturated with nitrogen gas. The solution was cooled and then stirred thoroughly with 10 ml of added enzyme solution containing 3061 units of glucoamylase (international standard units, pH 4.5, 40°C, with maltose as substrate). Portions of the resultant solution, each 5 ml in volume and containing 139 units of the enzyme, were injected in ampoules, which were then hermetically sealed in a current of nitrogen gas. The sealed ampoules were exposed to several M.rads of gamma rays at a dosage rate of $6.54 \times 10^4$ rads/hr so as to be gelled. After irradiation, the gelled products were removed from the ampoules, washed with water three times, drained, then weighed and tested for activity. The results thus obtained are shown in Table 1.

In the case of a dosage of 5 M.rads, there was obtained about 6.5 g of gel which was found to retain a total of 26.2 units of activity. This means that the gelation lowered the activity from the initial value of 139 units to 26.2 units, the recovery ratio of activity being 19%. According to this method of enzyme entrapping, substantially all the glucoamylase added was entrapped and immobilized and absolutely no enzyme leakage was observed.

Table 1

| Dosage | Weight of formed gel | Activity of added enzyme (A) | Activity of gelled enzyme (B) | Ratio of (B)/(A) |
| --- | --- | --- | --- | --- |
| 3 M.rad | 8.4 g | 139 unit | 26.5 unit | 19% |
| 4 M.rad | 10.1 | 139 | 22.5 | 16 |
| 5 M.rad | 6.5 | 139 | 26.2 | 19 |
| 6 M.rad | 6.1 | 139 | 22.3 | 16 |
| 7 M.rad | 6.2 | 139 | 21.7 | 16 |

The glucoamylase activity was determined by the following procedure: A total of 10 ml of the solution of substrate adjusted to have 1% maltose content and a pH value of 4.5 was shaken at 40°C for 30 minutes to induce the enzymatic reaction. At the end of said period, the reaction system was thermally inactivated and assayed for liberated glucose content.

The degree of enzyme leakage from the gelled product was determined as follows: A 1-g to 2-g sample of the gel was added to a solution consisting of 20 ml of 2% maltose solution and 20 ml of 1/100M acetic acid buffer solution (pH 4.5). The resultant mixture was shaken at 40°C for 60 minutes to induce a reaction. At the end of the reaction, the reaction system was filtered. The filtrate was subjected overnight to dialysis and the dialyzate was tested for residual enzymatic activity.

The procedure described above was repeated, except the ampoules were sealed under a pressure decreased to less than 1 mm Hg instead of in the current of nitrogen gas. Consequently, there were obtained substantially the same results as before.

EXAMPLE 2

A 10-ml solution containing 285,000 units of invertase (international standard units, pH 5.2, 40°C) was added to 10% aqueous solution of polyvinyl alcohol prepared similarly to Example 1. Portions of the resultant solution, each 5 ml in volume and containing 12,955 units of the enzyme, were injected into ampoules, which were then hermetically sealed in a current of nitrogen gas. The sealed ampoules were treated similarly to Example 1. The gels consequently formed therein were weighed and then tested for activity. Table 2 shows the results.

In the case of a dosage of 5 M.rads, there was obtained 3.9 g of gel, whose total activity was found to be 1,084 units. This means that the gelation lowered the activity from the initial value of 12,955 units to 1,084 units, the recovery ratio of activity being 8%. According to his method of enzyme entrapping, substantially all the invertase added was entrapped and immobilized and absolutely no leakage of invertase was observed.

Table 2

| Dosage | Weight of formed gel | Activity of added enzyme (A) | Activity of gelled enzyme (B) | Ratio of (B)/(A) |
| --- | --- | --- | --- | --- |
| 4 M.rad | 5.4 g | 12,955 unit | 1466 unit | 11% |
| 5 M.rad | 3.9 | 12,955 | 1084 | 8 |
| 6 M.rad | 4.9 | 12,955 | 828 | 6 |
| 7 M.rad | 3.8 | 12,955 | 783 | 6 |
| 8 M.rad | 3.8 | 12,955 | 646 | 5 |

The determination of the invertase activity was carried out by following the procedure of Example 1, except that sucrose was used as the substrate and the reaction was performed at a pH value of 5.2.

The determination of the degree of invertase leakage from the invertase gel was also carried out by following the procedure of Example 1, except that sucrose was used as the substrate and 1/200M phosphoric acid buffer solution was used in place of the acetic acid buffer solution.

EXAMPLE 3

A 10-ml solution containing 2,242 units of beta-galactosidase (international standard units, pH 4.5, 40°C, with lactose as substrate) was added to 10% aqueous solution of polyvinyl alcohol prepared similarly to Example 1. Portions of the resultant solution, each 5 ml in volume and containing 111 units of the enzyme, were injected into ampoules, which were then hermetically sealed in a current of nitrogen gas. The sealed ampoules were treated similarly to Example 1. The gelled products were weighed and then tested for activity. The results are shown in Table 3.

In the case of a dosage of 4 M.rads, there was obtained 5.8 g of gel, whose total activity was found to be 21 units. This means that the gelation lowered the activity from the initial value of 112 units to 21 units, the recovery ratio of activity being 19%. According to this method of enzyme entrapping, substantially all the beta galactosidase added was entrapped and immobilized and absolutely no leakage of betagalactosidase was observed.

Table 3

| Dosage | Weight of formed gel | Activity of added enzyme (A) | Activity of gelled enzyme (B) | Ratio of (B)/(A) |
| --- | --- | --- | --- | --- |
| 4 M.rad | 5.8 g | 111 unit | 20.9 unit | 19% |
| 5 M.rad | 5.1 | 111 | 11.8 | 11 |
| 6 M.rad | 4.6 | 111 | 7.5 | 7 |
| 7 M.rad | 4.3 | 111 | 5.9 | 5 |

The determination of the beta-galactosidase activity was carried out by following the procedure of Example 1, except that lactose was used as the substrate.

The determination of the degree of beta-galactosidase leakage was carried out by following the procedure of Example 1, except that lactose was used as the substrate.

EXAMPLE 4

A 10-ml solution containing 230 units of glucose isomerase (international standard units, 50°C, pH 7.0) was added to 10% aqueous solution of polyvinyl alcohol prepared similarly to Example 1. Portions of the resultant solution, each 5 ml in volume and containing 10.5 units of the enzyme, were injected into ampoules, which were then hermetically sealed in the current of nitrogen gas. The sealed ampoules were treated similarly to Example 1. The gels consequently formed therein were weighed and then tested for activity.

In the case of a dosage of 5 M.rads, there was obtained 4.6 g of gel, whose total activity was found to be 2.1 units. This means that the gelation lowered the enzyme activity from the initial value of 10.5 units to 2.1 units, the recovery ratio of activity being 21%. According to this method of enzyme entrapping, substantially all the glucose isomerase added was entrapped and immobilized.

The determination of glucose isomerase activity was carried out by the following procedure: First, 1 ml of enzyme solution or 1 ml of gel and distilled water were added to a reaction solution containing 3 ml of 0.1M phosphoric acid buffer solution, 0.5 ml of 0.1M $MgSO_4$ solution and 0.5 ml of 0.1M glucose solution and the resultant mixture was allowed to stand at 50°C for one hour to induce enzymatic reaction. At the end of 1 hour, 5 ml of 0.5M perchloric acid was added to the reaction system to stop the reaction. Then the system was assayed for fructose content by the cysteine-carbazole method.

EXAMPLE 5

A 10-ml solution containing 5,000 units of glucose oxidase (the enzyme activity capable of absorbing 10 μl of oxygen gas per minute at 30°C and pH 5.9 taken as unity) was added to 10% aqueous solution of polyvinyl alcohol prepared similarly to Example 1. Portions of the resultant solution, each 5 ml in volume and containing 228 units of the enzyme, were injected into ampoules, which were then hermetically sealed in a current of nitrogen gas. The sealed ampoules were treated similarly to Example 1. The gels formed consequently therein were weighed and then tested for activity.

In the case of a dosage of 5 M.rads, there was obtained 5.3 g of gel, whose total activity was found to be 63 units. This means that the gelation decreased the enzyme activity from the initial value of 228 units to 63 units, the recovery ratio of activity being 28%. According to this method of enzyme entrapping, substantially all the glucose oxidase was entrapped and immobilized.

The determination of glucose oxidase was carried out by the following procedure: Warburg's process was employed. In the main chamber, there were placed 1 ml of 1/10M acetate buffer (pH 5.9), 0.5 ml of distilled water and then 1 ml of enzyme solution or 1 ml of a mixture of gel with distilled water. In the side chamber, 0.5 ml of 4% glucose solution was place. Then, the temperature was preliminarily elevated to 30°C. The substrate in the side chamber was added to the main chamber contents to induce the enzymatic reaction, during which the absorption of oxygen gas was measured.

EXAMPLE 6

A 10-ml solution containing 20,000 units of catalase (the enzyme activity capable of generating 10 μl of oxygen gas per minute at 20°C at pH 4.5 taken as unity) was added to 10% aqueous solution of polyvinyl alcohol prepared similarly to Example 1. Portions of the resultant solution, each 5 ml in volume and containing 910 units of the enzyme, were injected into ampoules, which was then hermetically sealed in a current of nitrogen gas. The sealed ampoules were treated similarly to Example 1. The gels formed consequently in the ampoules were weighed and tested for activity.

In the case of a dosage of 5 M.rads, there was obtained 5.1 g of gel, whose total activity was found to be 320 units. This means that the gelation decreased the activity from the initial value of 910 units to 320 units, the recovery ratio of activity being 35%. According to this method of enzyme entrapping, substantially all the catalase added was entrapped and thoroughly immobilized.

The determination of catalase activity was carried out by the following procedure: Warburg process was employed. In the main chamber, there were placed 1 ml of 1/50M phosphoric acid buffer solution (pH 7.0) and 1 ml of catalase solution or 1 ml of the mixture of catalase gel with distilled water. In the side chamber was placed 1 ml of 5% $H_2O_2$ solution. The temperature was preliminarly elevated to 20°C. Then, the substrate of the side chamber was added to the main chamber contents to induce the enzymatic reaction, during which the generation of oxygen gas was measured.

EXAMPLE 7

In a nitrogen atmosphere, 10 g of polyvinyl alcohol was dissolved under heating in 90 ml of water saturated with nitrogen gas. The resultant solution was cooled and subsequently agitated thoroughly with 10 ml of added solution containing 1,354 units of glucoamylase (international standard units, pH 4.5, 40°C, with maltose as substrate). Then, portions of the solution, each 5 ml in volume and containing about 68 units of the enzyme, were injected into flat ampoules (18 × 220 mm), which were then hermetically sealed in the current of nitrogen gas. The sealed ampoules were exposed to electron rays of several mega.roentgens to have their contents gelled. In this case, the electron rays were generated from a linear accelerator, which was regulated so as to emit accelerated electron rays at 7.5-million electron volts and 49.5 microamperes to provide a radiation of 1.2 mega.roentgens per minute. After the irradiation, the gels formed consequently in the ampoules were removed, washed with water three times, drained sufficiently, weighed and then tested for activity. The results obtained are shown in Table 4.

In the case of a dosage of 6.0 mega.roentgens, for Example, there was obtained 5.75 g of gel, whose total activity was found to be 26.2 units. This means that the gelation decreased the enzyme activity from the initial value of 68 units to 26.2 units, the recovery ratio of activity being 39%. According to this method of enzyme entrapping, substantially all the glucoamylase was entrapped. Absolutely no leakage of the enzyme was observed.

Table 4

| Dosage | Weight of formed gel | Activity of added enzyme (A) | Activity of gelled enzyme (B) | Ratio of (B)/(A) |
| --- | --- | --- | --- | --- |
| (Roentgen) | | | | |
| 6.0××10⁶ | 5.75 g | 68 unit | 26.2 unit | 39% |
| 12.0×10⁶ | 3.74 | 68 | 19.1 | 28 |

The determination of the enzyme activity and that of the degree of enzyme leakage were carried out by following the procedure of Example 1.

EXAMPLE 8

A 10-ml solution containing 21,200 units of invertase (international standard units, 40°C, pH 5.2, sucrose as substrate) was added to 10% aqueous solution of polyvinyl alcohol prepared similarly to Example 1. The resultant solution was thoroughly agitated. Portions of the solution, each 5 ml in volume and containing about 1,060 units of the enzyme, were injected into flat ampoules, which were then hermetically sealed in a current of nitrogen gas. The irradiation was carried out under entirely the same conditions as described in Example 8. After the irradiation, the gels formed consequently in the ampoules were removed, washed with water three times, drained sufficiently, weighed and then tested for activity. The results obtained are shown in Table 5.

In the case of a dosage of 6.0 mega.roentgens, there was obtained 5.35 g of gel, whose total activity was found to be 342 units. This means that the gelation decreased the enzyme activity from the initial value of 1,060 units to 342 units, the recovery ratio of activity being 32%. According to this method of entrapping, substantially all the invertase added was entrapped. Absolutely no enzyme leakage was observed.

Table 5

| Dosage | Weight of formed gel | Activity of added enzyme (A) | Activity of gelled enzyme (B) | Ratio of (B)/(A) |
| --- | --- | --- | --- | --- |
| (Roentgen) | | | | |
| $6.0 \times 10^6$ | 5.35 g | 1060 unit | 342 unit | 32% |
| $12.0 \times 10^6$ | 3.14 | 1060 | 179 | 18 |

The determination of the activity and that of the degree of enzyme leakage were carried out by following the procedure of Example 2.

EXAMPLE 9

In a nitrogen atmosphere, 20 g of polyvinyl pyrrolidone was dissolved under heating in 80 ml of water saturated with nitrogen gas. The solution was cooled. A 10-ml solution containing 2,026 units of glucoamylase (normalized similarly to Example 1) was added to the cooled solution and diluted to a total volume of 110 ml. Portions of the resultant solution, each 5 ml in volume and containing 92.1 units of the enzyme, were injected into ampoules, which were then hermetically sealed in a current of nitrogen gas. The sealed ampoules were exposed to several mega.rads of gamma rays so as to be gelled. The gels formed consequently in the ampoules were removed, washed with water three times, drained sufficiently, weighed, and tested for activity. The results obtained are shown in Table 6.

In the case of a dosage of 3.8 M.rads, for Example, there was obtained about 13.3 g of gel, whose total activity was found to be 34.0 units. This means that the gelation decreased the enzyme activity from the initial value of 92.1 units to 34.0 units, the recovery ratio of activity being 37%. According to this method of enzyme entrapping, substantially all the glucoamylase added was entrapped and immobilized. Absolutely no leakage of glucoamylase was observed.

Table 6

| Dosage | Weight of formed gel | Activity of added enzyme (A) | Activity of gelled enzyme (B) | Ratio of (B)/(A) |
| --- | --- | --- | --- | --- |
| 3.0 M.rad | 15.4 g | 92.1 unit | 40.5 unit | 44% |
| 3.8 M.rad | 13.3 | 92.1 | 34.0 | 37 |
| 5.0 M.rad | 9.9 | 92.1 | 22.3 | 24 |
| 6.1 M.rad | 8.3 | 92.1 | 14.6 | 16 |

The determination of the activity of glucoamylase and that of the degree of the enzyme leakage were carried out by following the procedure of Example 1.

EXAMPLE 10

In a nitrogen atmosphere, 20g of polyvinyl pyrrolidone was dissolved under heating in 80 ml of water saturated with nitrogen gas. The solution was cooled. A 10-ml of solution containing 3,747 units of beta galactosidase (normalized similarly to Example 3) was added to the cooled solution and then diluted to a total volume of 110 ml. Portions of the resultant solution, each 5 ml in volume and containing 170.3 units of the enzyme, were injected into ampoules, which were then hermetically sealed in a current of nitrogen gas. The sealed ampoules were exposed to several mega.rads of gamma rays to have the contents gelled. After the irradiation, the gels formed consequently in the ampoules were removed, washed with water three times, drained sufficiently, weighed and then tested for activity. The results obtained are shown in Table 7. In the case of a dosage of 3.8 M.rads, there was obtained about 14.5 g of gel, whose total activity was found to be 31.4 units. This means that the gelation decreased the enzyme activity from the initial value of 170.3 units to 31.4 units, the recovery ratio of activity being 18%. According to this method of enzyme entrapping, substantially all the beta galactosidase added was entrapped and immobilized. Absolutely no leakage of beta galactosidase was observed.

Table 7

| Dosage | Weight of formed gel | Activity of added enzyme (A) | Activity of gelled enzyme (B) | Ratio of (B)/(A) |
| --- | --- | --- | --- | --- |
| 3.0 M.rad | 18.3 g | 170.3 unit | 38.2 unit | 22% |
| 3.8 M.rad | 14.5 | 170.3 | 31.4 | 18 |
| 5.0 M.rad | 11.4 | 170.3 | 21.3 | 13 |
| 6.1 M.rad | 9.4 | 170.3 | 14.5 | 9 |

The determination of the activity of beta galactosidase and that of the degree of the enzyme leakage were carried out by following the procedure of Example 3.

What is claimed is:

1. A method for the production of an immobilized enzyme, which comprises adding a radioresistant enzyme to the aqueous solution of a polyvinyl type high molecular compound selected from the group consisting of polyvinyl alcohol and polyvinyl pyrrolidone and irradiating the resultant mixture with ionizing radiant rays for thereby gelling the mixture.

2. A method according to claim 1, wherein the radioresistant enzyme is one member selected from the group consisting of glucoamylase, invertase, beta-galactosidase, glucose oxidase, glucose isomerase and catalase.

3. A method according to claim 1, wherein the amount of the enzyme to be added to the aqueous solution of polyvinyl type high molecular compound is in the range of from 0.001 to 5% by weight.

4. A method according to claim 1, wherein the ionizing radiant rays are one or more selected from the group consisting of beta rays, gamma rays or accelerated electron rays.

5. A method according to claim 4, wherein the dosage of the radiant rays is in the range of from 1 M.rad to 20 M.rads.

* * * * *